US010231628B2

(12) United States Patent
Guillemaud et al.

(10) Patent No.: US 10,231,628 B2
(45) Date of Patent: Mar. 19, 2019

(54) METHOD FOR MEASURING MOVEMENTS OF A PERSON WEARING A PORTABLE DETECTOR

(75) Inventors: Regis Guillemaud, La Tronche (FR); Yanis Caritu, St. Joseph de Riviere (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 374 days.

(21) Appl. No.: 11/962,944

(22) Filed: Dec. 21, 2007

(65) Prior Publication Data
US 2008/0214963 A1 Sep. 4, 2008

Related U.S. Application Data

(63) Continuation-in-part of application No. 10/879,303, filed on Jun. 30, 2004, now abandoned.

(30) Foreign Application Priority Data

Jul. 2, 2003 (FR) .................................... 03 50285

(51) Int. Cl.
*A61B 5/0205* (2006.01)
*A61B 5/11* (2006.01)
(Continued)

(52) U.S. Cl.
CPC ........ *A61B 5/0205* (2013.01); *A61B 5/02444* (2013.01); *A61B 5/113* (2013.01);
(Continued)

(58) Field of Classification Search
CPC .......... A61B 2562/0219; A61B 5/7203; A61B 5/1123; A61B 5/1118; A61B 5/1116; A61B 5/0205
(Continued)

(56) References Cited

U.S. PATENT DOCUMENTS

| 4,338,950 A | 7/1982 | Barlow et al. |
| 5,354,317 A | 10/1994 | Alt |

(Continued)

FOREIGN PATENT DOCUMENTS

| WO | WO 02/061704 | 8/2002 |
| WO | WO 03/005893 | 1/2003 |

*Primary Examiner* — Rene Towa
*Assistant Examiner* — H. Q. Nguyen
(74) *Attorney, Agent, or Firm* — Oblon, McClelland, Maier & Neustadt, L.L.P.

(57) ABSTRACT

A process for detecting activity of a person, in which movements of the person are measured by at least one sensor attached to the person, and respective components of the movements due to external activity and due to physiological activity are separated. The process obtains a signal of the sensor, filters the signal to derive a filtered signal, the filtering including partitioning the signal of the center into a low frequency component and high frequency component, and subtracts the filtered signal from the signal of the sensor. The filtering further variably extracts portions of the high frequency component according to a criterion of either a minimal level or a minimal instability of the signal of the sensor, and the filtered signal includes the low frequency component and the extracted portions of the high frequency components.

16 Claims, 2 Drawing Sheets

(51) Int. Cl.
*A61B 5/113* (2006.01)
*A61B 5/00* (2006.01)
*A61B 5/024* (2006.01)

(52) U.S. Cl.
CPC ........... *A61B 5/1116* (2013.01); *A61B 5/1118* (2013.01); *A61B 5/1123* (2013.01); *A61B 5/7214* (2013.01); *A61B 5/02438* (2013.01); *A61B 5/6823* (2013.01); *A61B 2562/0219* (2013.01)

(58) Field of Classification Search
USPC ............................................ 600/595; 607/19
See application file for complete search history.

(56) References Cited

U.S. PATENT DOCUMENTS

| | | |
|---|---|---|
| 5,360,436 A | 11/1994 | Alt et al. |
| 5,935,081 A | 8/1999 | Kadhiresan |
| 6,477,421 B1 | 11/2002 | Andersen et al. |
| 6,491,647 B1 | 12/2002 | Bridger et al. |
| 6,522,266 B1 | 2/2003 | Soehren et al. |
| 6,734,834 B1 | 5/2004 | Baram |
| 2002/0008630 A1 | 1/2002 | Lehrman et al. |
| 2002/0062204 A1* | 5/2002 | Nakajima ................... 702/150 |
| 2003/0163177 A1 | 8/2003 | Eggers et al. |
| 2004/0010210 A1 | 1/2004 | Avinash et al. |
| 2005/0101889 A1* | 5/2005 | Freeman et al. ................ 601/41 |

\* cited by examiner

METHOD FOR MEASURING MOVEMENTS OF A PERSON WEARING A PORTABLE DETECTOR

CROSS-REFERENCE TO RELATED APPLICATIONS

The present application is a continuation-in-part of U.S. application Ser. No. 10/879,303 filed on Jun. 30, 2004, and in turn claims priority to French application 0350285 filed on Jul. 2, 2003, the entire contents of each of which are hereby incorporated herein by reference.

BACKGROUND OF THE INVENTION

Field of the Invention

The subject of this invention is a method to measure the movements of a person wearing a portable detector.

Discussion of the Background

There is a very wide variety of prior art for measuring heart or other signals using a detector that is attached to a patient. Movement sensors such as accelerometers have thus been proposed to monitor movements of the thorax cage and to deduce the heart rate from these movements. However, this type of detector has been reserved for particular conditions or postures of the patient; in general, a lack of effort or movement is necessary to give a reliable measurement, that is not confused by components from sources other than the movement signal, and that could be preponderant due to the small amplitude of movements originating from the heart.

Movement sensors at various locations of the body have also been applied to monitor persons wearing the detector and sometimes to determine a state of sleep, a fall, etc. The complexity of postures and levels of human activity makes a real analysis of the activity difficult when using usual detectors, which are reserved particularly for the detection of a single type of event and are programmed to ignore other events, as far as possible.

SUMMARY OF THE INVENTION

For example, it would be useful to complete a fall detector with a physiological measurements detector to check the state of the patient after the fall, but this would be only possible if the patient wears two corresponding detectors, which is uncomfortable.

The invention proposes an improved portable detector, in which a more accurate distinction between a signal component due to an external activity of the wearer and at least one signal component due to a physiological activity (heart beats or breath in particular) is made than in the prior art.

The purposes of the invention are to:
supply a detector making a distinction between signal components with clearly different levels and that can vary strongly with time;
doing the above, starting from measurements made by the same movement sensors;
provide such a detector with a unit structure and that is compact;
offer an increased capacity for measurement and diagnosis of physiological states, limiting the durations in which measurements must not be considered;
offer a more universal determination of posture and activity states of the wearer, and discern a larger number of them.

Heart beats and breathing are periodic movements, for which the intensity and frequency vary depending on the activity level of the wearer under particular conditions. Movements due to the external activity of the wearer are usually low frequency; but since they are not periodic, they cover a wider frequency range, and their intensity can vary strongly.

Devices and corresponding processes of the prior art isolate an estimation of the physiological activity by successive filterings of noise (at higher frequencies, with a low-pass filter) and outer physical activity (with a high pass filter). A signal supposed to correspond to the physiological activity is obtained after this. Unfortunately, mere signal filterings are unlikely to provide reliable results as the physical activity often comprises a part of the energy in the same frequencies as the physiological activity, especially in transient postural states or when great efforts are exerted. The physical energy being often greater in these unfavorable circumstances, the amount due to physiological activity is all the more blurred.

Incorrect detection that can lead to a false alert should be avoided. This type of situation can arise with some particularly sudden external movements that actually prevent satisfactory detection of physiological movements. One aspect of this invention accordingly is embodied in a process that reduces or eliminates the influence of an unfiltered physical activity in the frequency band where physiological activity is present.

Another difficulty is the sensitivity of measurements to the body posture adopted by the wearer, since the acceleration due to gravity which is involved in accelerometric measurements and that has to be corrected, is perceived with an intensity that depends on this posture, and since measurements of the physiological activity give much lower acceleration values. It is recommended that wearer position indicators should be added, particularly magnetometers measuring the direction of the ambient magnetic field in order to clearly determine the posture of the wearer and to choose only some of the movement signals, while eliminating signals that are excessively affected by gravity, for treatment according to the invention. This improvement is useful particularly when several sensors measure different wearer movements in different directions. One frequent situation consists of using three sensors, measuring movements in perpendicular directions, usually one forward movement, one sideways movement and one upward movement of the person.

BRIEF DESCRIPTION OF THE DRAWINGS

One embodiment of the invention will now be described more completely with reference to the figures.

DESCRIPTION OF THE PREFERRED EMBODIMENTS

Figure 1:
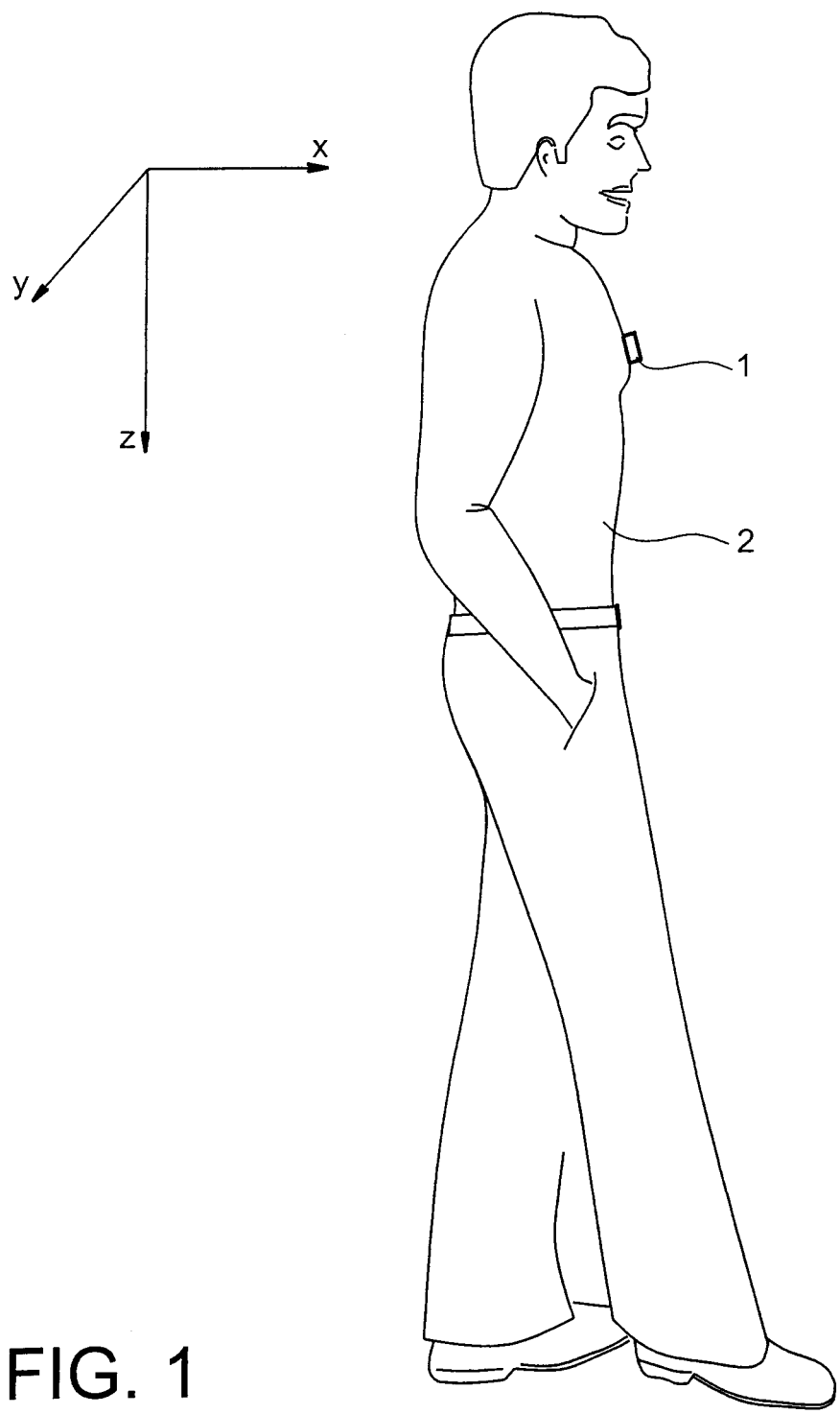
FIG. 1 illustrates the position of the detector on the wearer.

FIG. 1 shows that the detector marked as reference 1 is placed on the chest of the wearer 2. It could be placed on the abdomen or elsewhere. The detector 1 is miniature so that, unlike others, it can be worn comfortably almost unperceived. The X, Y and Z axes are introduced to facilitate the explanation and define a coordinate system related to the wearer 2, the X axis being in the forward direction, the Z axis being downwards towards the wearer's feet, and the Y axis is being towards the right.

Figure 2:
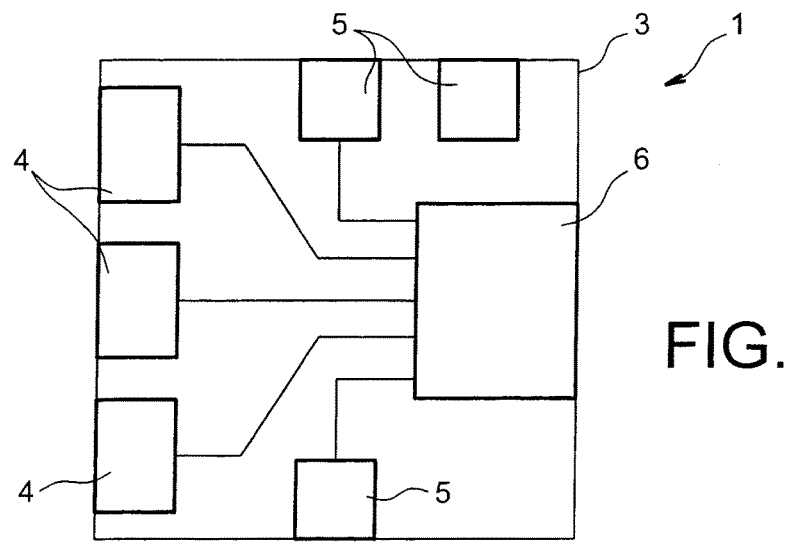
FIG. 2 shows the detector as a whole.
Figure 3:
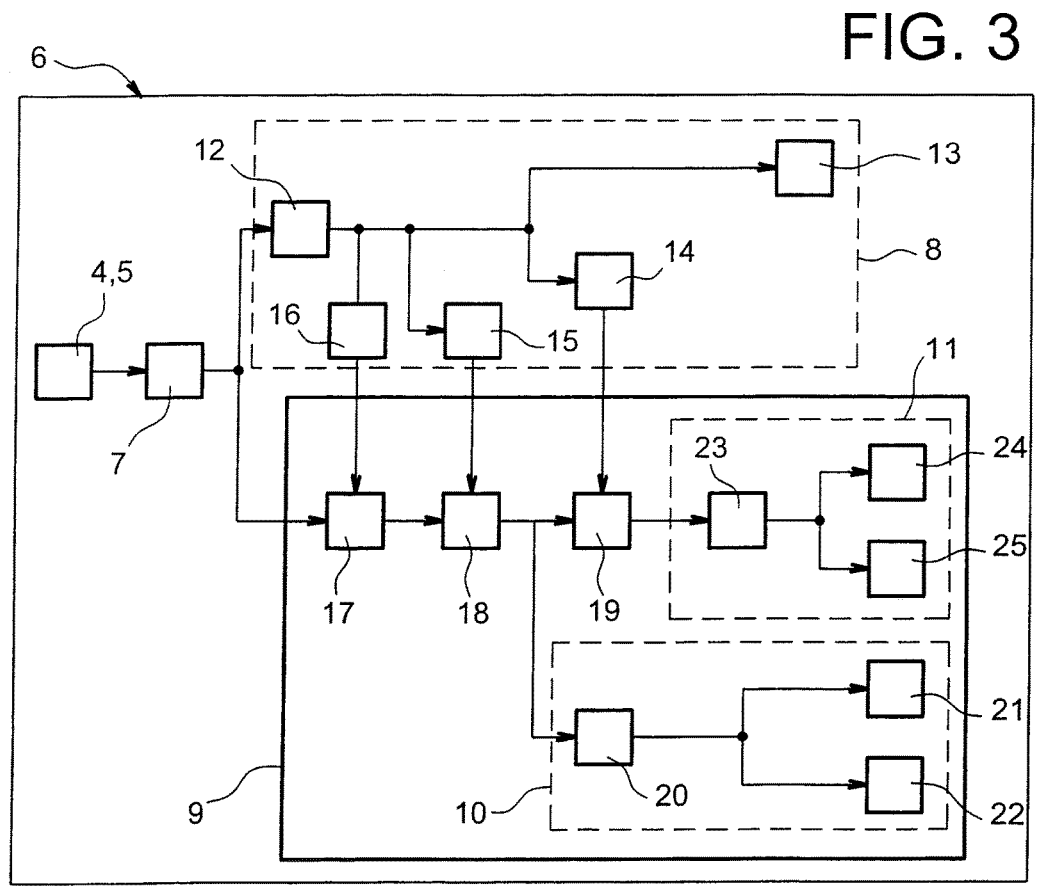
FIG. 3 shows the processing system.

According to FIG. 2, the detector 1 may comprise a unit 3 containing three accelerometers all marked as reference 4, three magnetometers all marked as reference 5, and a processing system 6 to which the accelerometers 4 and magnetometers 5 are connected by wires through which their signals are carried to it. Each accelerometer 4 measures an acceleration component of the chest movement of the wearer 2 along one of the X, Y and Z axes, as a function of the direction of gravity; the magnetometers 5 do the same thing as a function of the direction of the earth's magnetic field. The detector 1 is kept at a constant orientation in contact with the skin or clothing of the wearer 2 by glue, a seam, a clamping strip or any other suitable means. The processing unit 6 will now be described with reference to FIG. 3.

The signals output from the accelerometers 4 or magnetometers 5 each pass through a normalization module 7 and are transmitted to two calculation modules 8 and 9 working in parallel and in interaction, the first 8 of which calculates the component of the signals due to external activity of the wearer 2, and the second 9 of which calculates the component of the signals due to the physiological activity; this second module 9 comprises a sub-module 10 assigned to movements due to heart beats and a sub-module 11 assigned to movements due to breathing.

The first calculation module 8 comprises a low pass filter 12 that transmits the signal output from the normalization module 7 to an activity analysis device 13, to a posture analysis device 14, an activity level analysis device 15 and a device 16 for estimating the activity component. The signal output from the normalization module 7 reaches sub-modules 10 and 11 after passing through a subtractor 17, a validation module 18 and also a selection device 19 for the sub-module 11. The sub-module 10 comprises a device for extraction of the heart component 20, a frequency calculation device 21 and an examination device 22. The sub-module 11 comprises a device for extraction of the breathing component 23, a device for the frequency calculation 24 and an output device 25.

These various elements will be described in sequence and in detail. The normalization device 7 is of an ordinary type that is used to calibrate the signals, for example according to a linear law, to supply normalized output signals that are proportional to the acceleration applied to them. The low pass filter 12 is used to eliminate signal high frequencies that in practice only express noise. The activity analysis device 13 is not indispensable and its content may depend on the activity types to be diagnosed, such as a fall, sleep, walking, position change or others. The diagnosis can be made with several sensors 4 and 5. The posture analysis device 14 can determine if the wearer 2 is standing up, seated or lying down, by comparing accelerations measured by accelerometers 4. If the largest signal is measured by the accelerometer 4 along X or the accelerator 4 along Y, the wearer is lying down, but the acceleration along Z will be preponderant if the wearer 2 is seated or standing, since gravity acts along this axis. The posture diagnosis is made if the acceleration ratios are higher than some specific coefficients. If the wearer 2 is standing up, the comparison of measurements for magnetometers 5 along X and Y can give its direction along the cardinal points. A fall can be determined if a fast rotation is detected about a vertical axis or a fast acceleration in rotation with respect to the field of gravity (measured with an accelerometer). Other criteria can easily be deduced for other postures.

The activity level analysis device 15 is designed to indicate if the activity of the wearer 2 reaches a level beyond which it is considered to be impossible to obtain the results for the physiological measurements correctly. It may consist of a bypass filter applied to signals from sensors 4 and 5 and produces a binary output. If the derived signal is more than a threshold, which is the result of an excessively sudden movement variation, the device 15 supplies an output equal to zero, and otherwise the output is equal to one. Another way of proceeding would be to apply a sliding criterion on differentiated signals originating from the sensors, according to the following formula:

CRI=(Abs [d(t)−d(t−k)])Sign[d(t)·d(t−k)] where CRI is the criterion, Abs is the absolute value operator, d is the derivative according to time of the signals originating from a sensor, t is the time, k is a predefined constant and Sign is the sign operator; +1 if the product [d(t)·d(t−k)] is positive, −1 if it is negative. The first part of the formula determines the level of CRI, the second part its sign; the device 15 will have a zero output if the calculation result of CRI is less than a negative threshold, which corresponds to a fast inversion of the movement direction, and otherwise the output will be equal to one.

When the signal from device 15 is zero, the validation module 18, which is a multiplier, outputs a null signal and therefore inhibits calculations of the physiological activity; otherwise, when the device 15 outputs a signal equal to 1, the validation module 18 has no influence over the signal passing through it and allows it to pass through without modifying it.

The purpose of the estimating device 16 is to isolate a component of the signal from each sensor 4 or 5 representative of the wearer's activity. It is according to the invention a non-stationary filter that avoids filtering the signal in the presence of a singular point of the signal corresponding to a fast inversion of its movement.

A filter F using a sigmoid function may be used. This process is based on the concept that the signal may be filtered without any disadvantage when it is stable, but it must not be filtered in highly unstable situations in which the wearer's activity also includes higher frequency movements.

A sigmoid function comprises to asymptotes, at 1 for high input values, at 0 for low input values, for zero and negative values in the present case.

According to the above, a filter F on the input signal denoted S(t) may be a low pass filter Flp weighted by the criterion CRI mentioned above:

$$F[S(t)]=[\text{sigmoid}(CRI)] \cdot S(t)+(1-\text{sigmoid }(CRI)) \times Flp [S(t)].$$

Thus, when CRI is positively large, the filter F in the estimating devices 16 outputs a result close to S(t), in other words, it has hardly an effect. When CRI is near zero or negatively large, the filter F outputs a result close to Flp [S(t)]. In other words which contains the low frequencies only of S(t). When CRI is intermediate, only a part of the high frequencies of S(t) is removed.

Filter functions other than F may also be applied, or filters capable of extracting a low frequency component of the signal that maintains discontinuities. Another recommended example of a filter is that mentioned in the article "Non linear anisotropic filtering of MRI data" IEEE Transactions on Medical Imaging, vol. 11, No. 2, p. 231-232 by G. Gerig.

The subtractor 17 has a positive terminal into which the normalized signal is input, and a negative terminal into which the signal output by the estimating device 16 is input. The difference corresponds to the signal representing the physiological activity. The subtraction with the above-mentioned filter entails the following characteristics. When the movement is comparatively stable, which corresponds to (d(k)−d(t−k))≈0 and CRI≈0, the result of the subtraction is a signal containing the high frequencies only of S(t). When the movement is unstable, Abs (d(t)−d(t−k)) is positively high, and so is CRI generally, the result of the subtraction is a signal which only contains a part of the high frequencies of S(t), the remaining part having been removed or extracted, and still no low frequencies. This corresponds to situations in which the movement due to the physical activity comprises components at high frequencies that superimpose over physiological activity at the same frequencies. Keeping a part of the high frequencies of S(t), the smaller when unstability is greater, avoids to overestimate the physiological activity and to issue a false diagnosis. Also, signals S of higher levels tend to yield higher values of Abs (d(t)−d(t−k)), so that the movement level has a similar effect on filtering that unstability. In less frequent situations with an inversion of the movement, Sign [d(t)·d(t−k)] becomes negative and CRI may become negatively large. It is deemed that no valid conclusion can be found from the sensor measurements then, and as we have seen, the validation module 18, which is a multiplier that leaves the subtraction result unchanged under circumstances considered to be normal, and this result now. The selection device 19 is used to choose the subtraction results that are the most representative of the breathing movement as a function of the posture of the wearer 2 estimated by the posture analysis device 14. If the wearer 2 is lying down, the movements due to breathing will be estimated by accelerometers 4 sensitive along the Y and Z directions, and by magnetometers 5 along the X and Z directions; otherwise, when the wearer 2 is seating or standing, accelerometers 4 will be considered along the X and Z directions and magnetometers 5 will be considered along the Y and Z directions. This provides a means of eliminating accelerometers influenced by the acceleration due to gravity that would supply excessively noisy measurements.

The heart rate extractor 20 is a low pass filter for which the limits may for example be 0.5 Hertz and 3 Hertz. The heart frequency calculation device 21 advantageously uses accelerometers 4 and particularly the accelerometer oriented along the X direction. The period is calculated by detecting consecutive maximums and estimating the durations that separate them. These maximums are produced by the main heart beat; they are about 30 milliseconds wide and are separated on average by a period of about 0.8 seconds for a person at rest. Detection may be improved by applying filtering adapted to the shape of the maximums to be detected, for example a filter with an equivalent width of 250 milliseconds which is a value equal to 1 at the center on an equivalent width of 30 milliseconds, and 0 at the periphery. The heart rate is equal to the inverse of the duration separating the maximums. A sliding average calculation can be made using the average of a few previously measured frequencies into consideration.

The output device 22 is usually a transmitter directing the results obtained towards a display or diagnosis device external to the detector 1.

The breathing component extraction device 23 also comprises a low pass filter between frequencies for example equal to 0.03 Hertz and 1 Hertz. The breathing rate calculation device 24 uses the results from one or several sensors 4 and 5 and calculates the breathing rate by estimating the duration between three consecutive passages of a breathing signal through zero; the rate is the inverse of this duration. In this case, a sliding average calculation can be carried out to improve the results, or an average of the calculation can be made on several sensors 4 and 5. Finally, the output device 25 still transmits results obtained towards an external display or diagnosis means, or a means of synchronizing another instrument on the breathing cycle.

There is no need to place six movement sensors in the detector 1 to use the invention, but it is quite obvious that the measurement of movements in all directions by two series of sensors with different references would give more universal results.

These magnetometers could be differential probes (fluxgates) or giant magneto-resistances.

In another embodiment, the detector comprises several sensors, for example distributed at different locations of the body, each sensor being connected to the signal processing unit 6, for example by an electrical connection, by radiofrequency. The advantage of this embodiment is that it overcomes the inability of a sensor to give physiological information, for example if the patient is leaning on a sensor, so that the sensor can no longer measure breathing. The other sensors located elsewhere are used. The number of sensors used, their degree of redundancy and their locations are not critical.

The invention claimed is:

1. A process for detecting an external activity signal and a separated physiological activity signal of a person, the process comprising:

obtaining a signal from a sensor measuring movements of a person to which the sensor is attached, the signal composed of a first component due to physiological activity of the person and a second component due to external activity of the person;

repeatedly computing a value of a criterion of either a minimal level or a minimal instability of the signal obtained from the sensor; and filtering, in a filter, the signal from the sensor to derive a filtered signal representative of the person's external activity, the filtering comprising a partition of the signal from the sensor into a low frequency component and a high frequency component, the filtered signal comprising the low frequency component of the signal of the sensor and a portion of the high frequency component, the portion being variable in the signal obtained from the sensor and depending, in each time portion of the filtered signal, on the value of the criterion, the portion of the high frequency component being greater when either the minimal level or the minimal instability of the signal of the sensor is reached; and subtracting the filtered signal from the signal obtained from the sensor, to obtain the first component of the signal due to physiological activity separated from the external activity signal.

2. A process according to claim 1, wherein the portion of the high frequency component results from a variable weighting of the high frequency component according to the criterion.

3. A process according to claim 2, wherein the filtered signal is expressed by α·S+(1−α) Flp(S), in which S is the signal obtained from the sensor, Flp(S) is a low pass filtering of the signal obtained from the sensor, and a is a variable weighting coefficient associated either to the level of the signal obtained from the sensor or to the instability of the signal obtained from the sensor.

4. A process according to claim 1, wherein the criterion of a minimal instability of the signal obtained from the sensor is estimated according to inversions of direction of movements between two instants separated by a determined duration.

5. A process according to claim 1, wherein the obtaining a signal from the sensor obtains signals along X, Y, and Z axes as a function of a direction of gravity and as a function of earth's magnetic field.

6. A process according to claim 1, further comprising determining a posture of the person, and controlling the subtracting based on the determined posture.

7. A process according to claim 6, wherein the determining the posture of the person determines whether the person is standing up, seated, or lying down.

8. A process according to claim 1, further comprising outputting the component of the signal due to physiological activity to a display device or diagnosis device external to the sensor.

9. A process for detecting an external activity signal and a separated physiological activity signal of a person, the process comprising:
    obtaining a signal from a sensor measuring movements of a person to which the sensor is attached, the signal composed of a first component due to physiological activity of the person and a second component due to external activity of the person;
    repeatedly computing a value of a criterion of a minimal instability of the signal obtained from the sensor; and
    filtering, in a filter, the signal from the sensor to derive a filtered signal representative of the person's external activity, the filtering comprising a partition of the signal from the sensor into a low frequency component and a high frequency component, the filtered signal comprising the low frequency component of the signal of the sensor and a portion of the high frequency component, the portion being variable in the signal obtained from the sensor and depending, in each time portion of the filtered signal, on the value of the criterion, the portion of the high frequency component being greater when the minimal instability of the signal of the sensor is reached; and
    subtracting the filtered signal from the signal obtained from the sensor, to obtain the first component of the signal due to physiological activity separated from the external activity signal.

10. A process according to claim 9, wherein the portion of the high frequency component results from a variable weighting of the high frequency component according to the criterion.

11. A process according to claim 10, wherein the filtered signal is expressed by $\alpha \cdot S + (1-\alpha) Flp(S)$, in which S is the signal obtained from the sensor, $Flp(S)$ is a low pass filtering of the signal obtained from the sensor, and a is a variable weighting coefficient associated either to the level of the signal obtained from the sensor or to the instability of the signal obtained from the sensor.

12. A process according to claim 9, wherein the criterion of a minimal instability of the signal obtained from the sensor is estimated according to inversions of direction of movements between two instants separated by a determined duration.

13. A process according to claim 9, wherein the obtaining a signal from the sensor obtains signals along X, Y, and Z axes as a function of a direction of gravity and as a function of earth's magnetic field.

14. A process according to claim 9, further comprising determining a posture of the person, and controlling the subtracting based on the determined posture.

15. A process according to claim 14, wherein the determining the posture of the person determines whether the person is standing up, seated, or lying down.

16. A process according to claim 9, further comprising outputting the component of the signal due to physiological activity to a display device or diagnosis device external to the sensor.

* * * * *